United States Patent [19]

Korenaga

[11] Patent Number: 4,676,246

[45] Date of Patent: Jun. 30, 1987

[54] LOW-FREQUENCY ELECTROTHERAPY APPARATUS

[76] Inventor: Tetsuya Korenaga, 8-17, Heiwa 3-chome, Chuo-ku, Fukuoka, Japan

[21] Appl. No.: 697,936

[22] Filed: Feb. 4, 1985

[51] Int. Cl.[4] .......................... A61F 7/00; A61N 1/32
[52] U.S. Cl. .................................. 128/399; 128/402; 128/783; 128/802; 128/803
[58] Field of Search ...................... 128/24.1, 82.1, 362, 128/399–400, 402, 403, 783, 798, 799, 802, 803; 219/209, 211

[56] References Cited

U.S. PATENT DOCUMENTS

| 658,601 | 9/1900 | Timar | 128/399 |
| 1,391,762 | 9/1921 | Dequer | 128/402 X |
| 1,594,053 | 7/1926 | Evans | 128/402 X |
| 2,718,585 | 9/1955 | Hariu | 128/402 X |
| 3,178,559 | 4/1965 | Fogel et al. | 128/399 X |

FOREIGN PATENT DOCUMENTS

| 1171095 | 5/1964 | Fed. Rep. of Germany | 128/783 |
| 1177263 | 9/1964 | Fed. Rep. of Germany | 128/362 |

Primary Examiner—Lee S. Cohen
Attorney, Agent, or Firm—Jordan and Hamburg

[57] ABSTRACT

A low-frequency electrotherapy apparatus has an electrotherapy pack adapted to fit on an affected part of the patient's body and a main controlling part to which the electrotherapy pack is connected through a cable. Necessary curing instruments such as directors, heater, wet pack and so forth are assembled together and built in the fitting unit.

4 Claims, 20 Drawing Figures

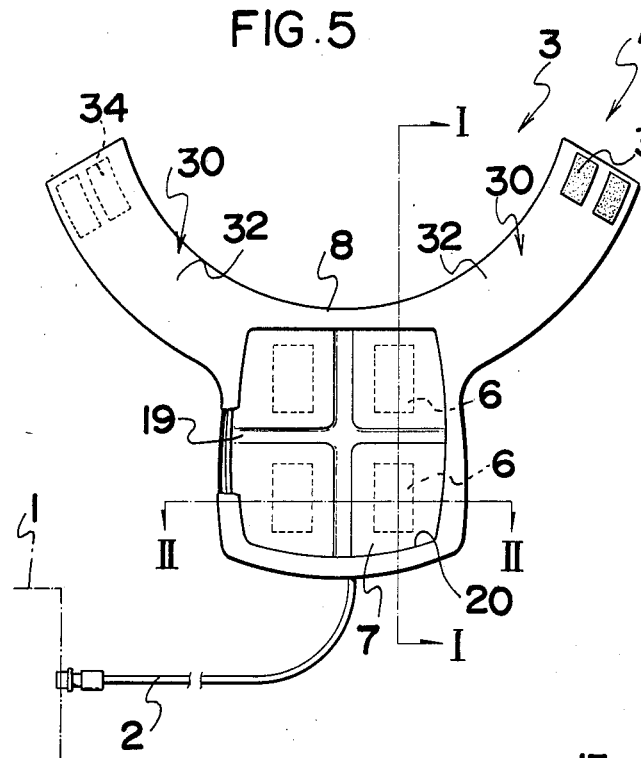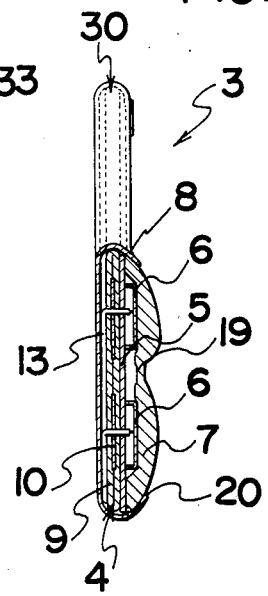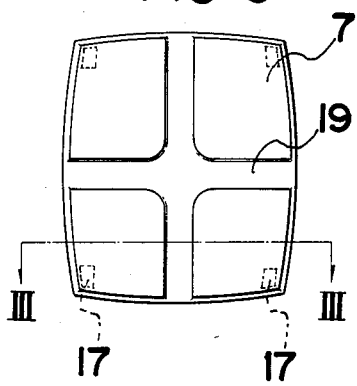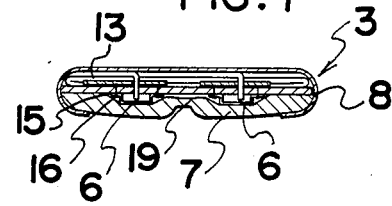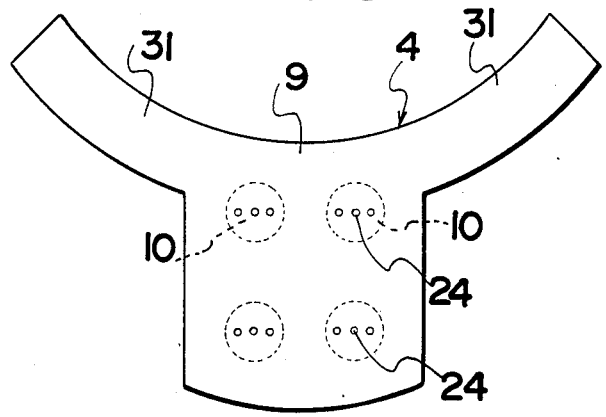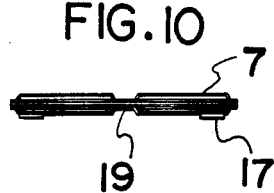

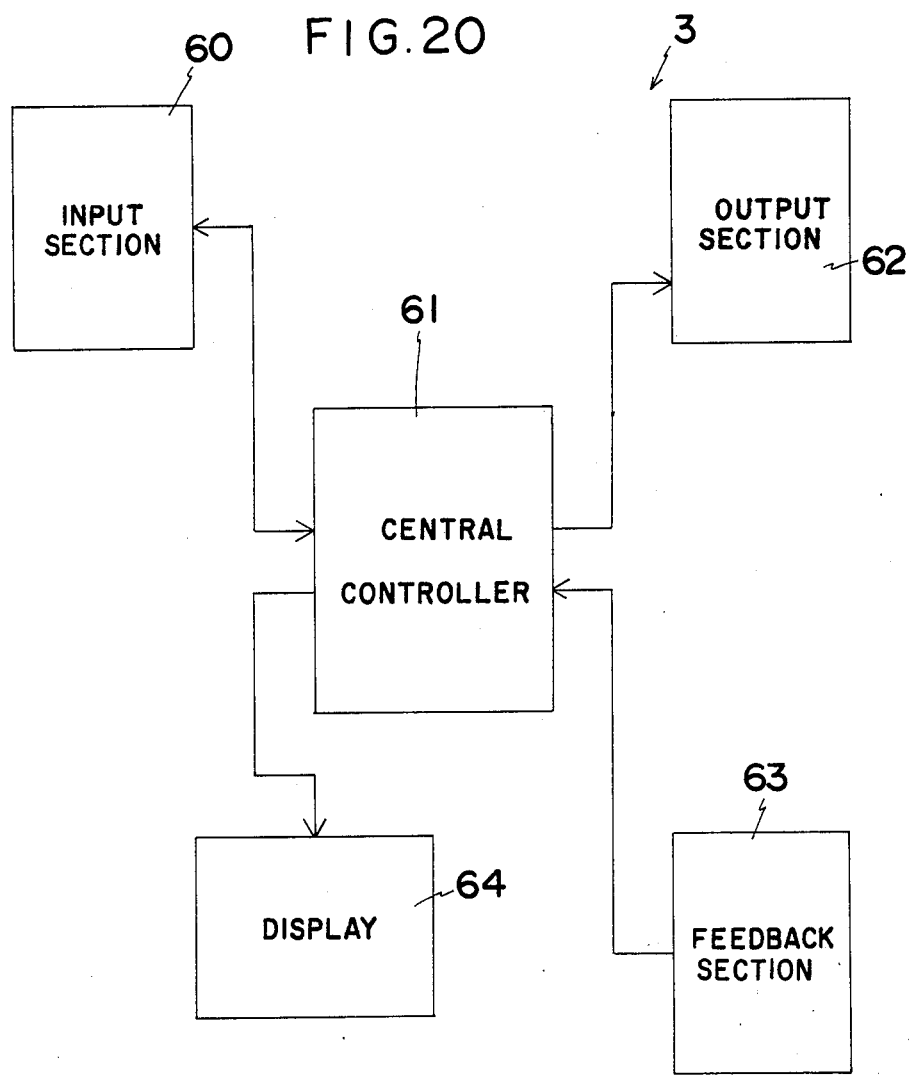

LOW-FREQUENCY ELECTROTHERAPY APPARATUS

BACKGROUND OF THE INVENTION

1. Field of the Invention

The present invention relates to a low-frequency electrotherapy apparatus having an electrotherapy pack in which a plurality of therapeutic devices such as a electrodes, heater and a wet pack are built into a single unit.

2. Description of the Prior Art

A known low-frequency electrotherapy apparatus has various components such as electrodes, a heater, and a wet pack which are prepared as separate components. During treatment, the wet pack is placed on the affected part of the patient, and the electrodes and the heater are stacked in the mentioned order on the wet pack. These therapeutic devices, however, are separate components and are provided with their own means of attachment such as belts for fixing them on the affected part of the patient's body. Thus, the conventional low-frequency therapeutic apparatus requires the troublesome task of fixing these independent parts one by one on the affected part of the patient's body.

SUMMARY OF THE INVENTION

To obviate the above-described problem of the prior art, the invention proposes an electrotherapy pack in which all necessary devices are built in.

Namely, the invention provides a low-frequency electrotherapy apparatus having an electrotherapy pack in which all necessary parts are built in, so that the apparatus can be applied to the affected part of the patient's body in a single fitting.

BRIEF DESCRIPTION OF THE DRAWINGS

FIG. 5 is a front elevational view of a second embodiment of the invention;

FIG. 6 is a sectional view taken along the line I—I of FIG. 5;

FIG. 7 is a sectional view taken along the line II—II of FIG. 5;

FIG. 8 is a front elevational view of a mounting plate in the second embodiment;

FIG. 9 is a front elevational view of a wet pack in the second embodiment;

FIG. 10 is a sectional view taken along the line III—III of FIG. 9;

FIG. 20 is a block diagram of an electrotherapy apparatus embodying the present invention.

DESCRIPTION OF THE PREFERRED EMBODIMENTS

Preferred embodiments of the invention will be described hereinunder with reference to the accompanying drawings.

Figure 1:
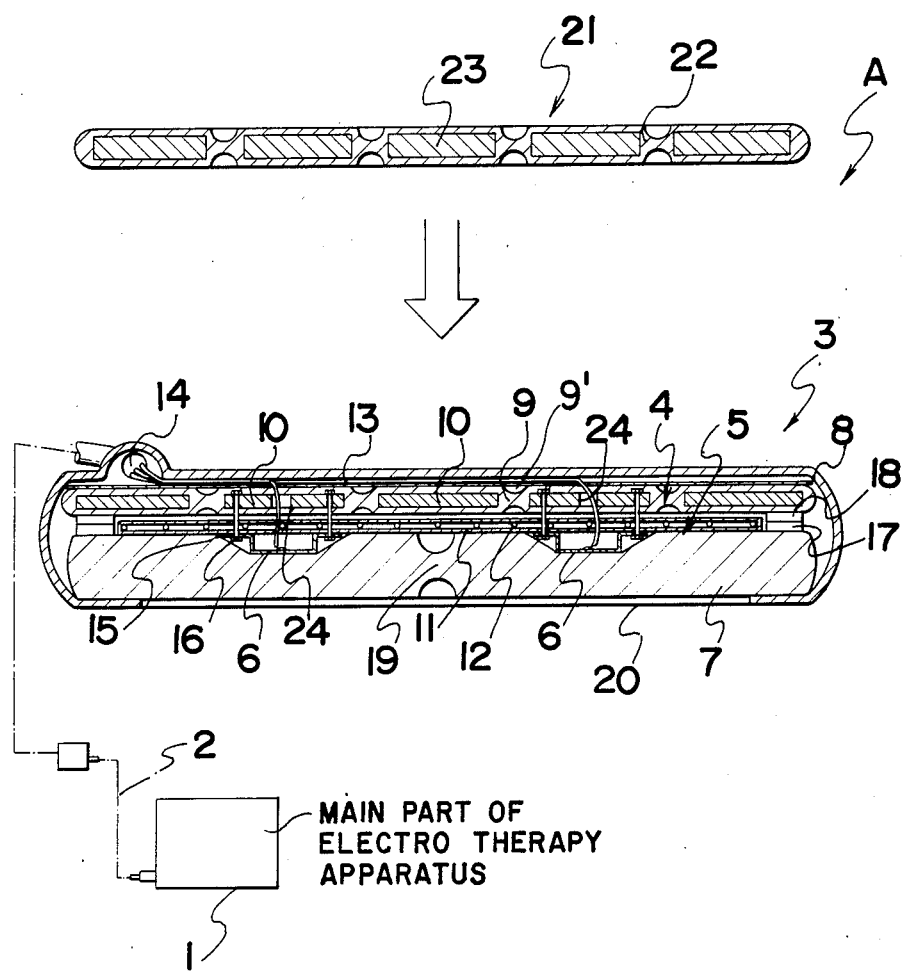
FIG. 1 is a longitudinal sectional view of a first embodiment of the invention.
Figure 2:
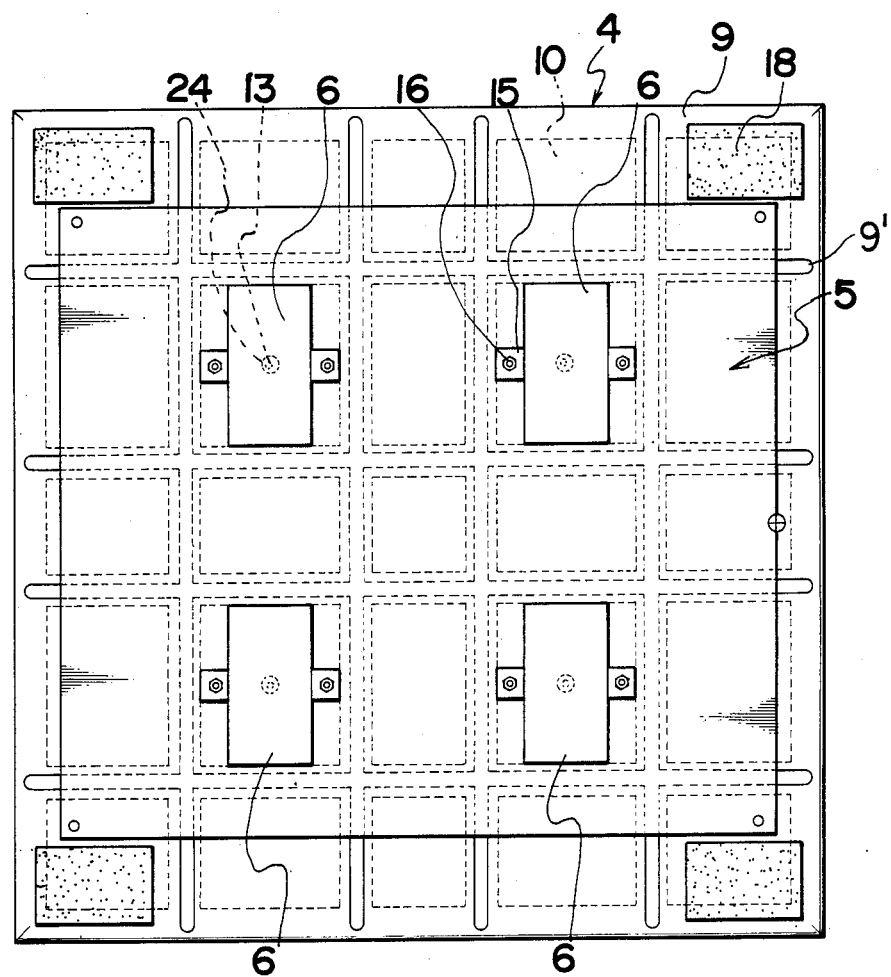
FIG. 2 is a bottom plan view of the first embodiment showing how a substrate, heater and an electrode are attached.
Figure 3:
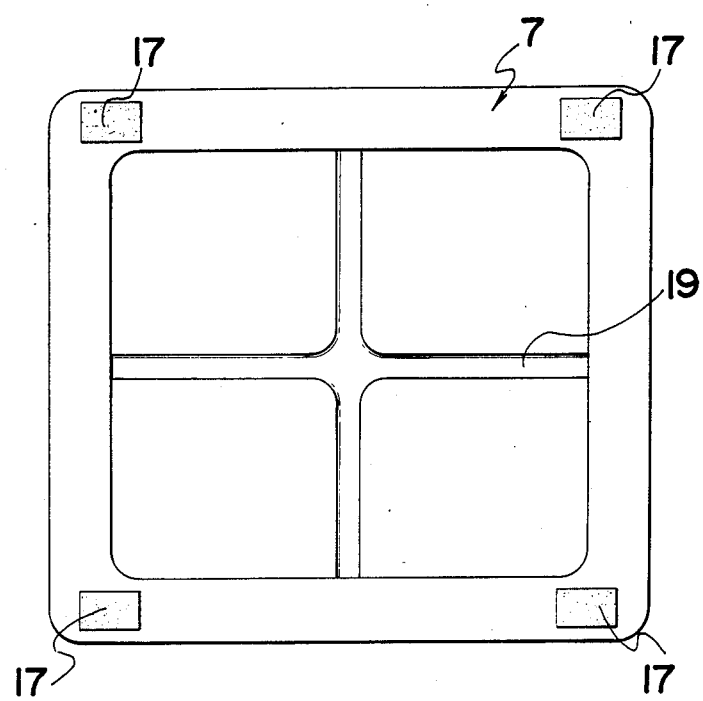
FIG. 3 is a plan view of a wet pack incorporated in the first embodiment.
Figure 4:
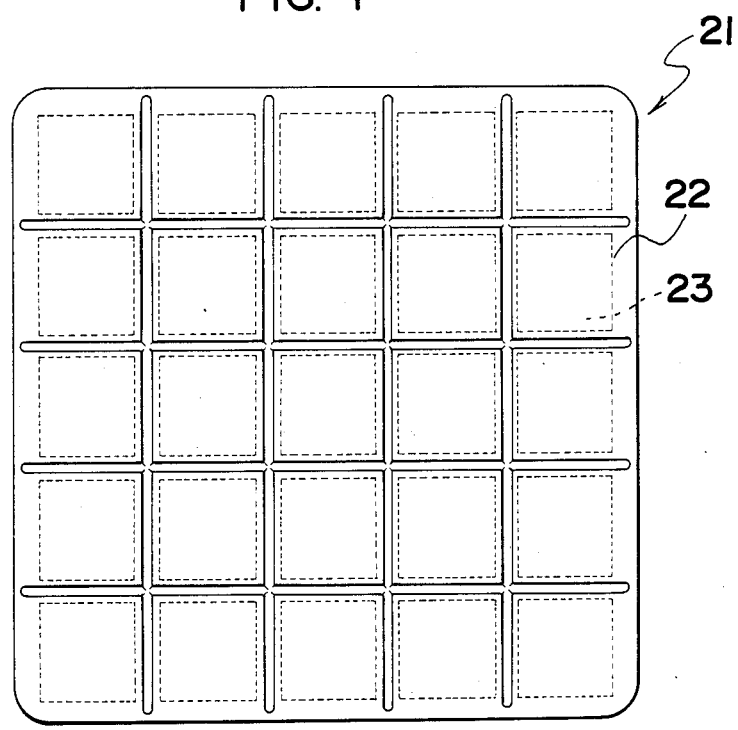
FIG. 4 is a plan view of a lap plate in the first embodiment.
Figure 11:
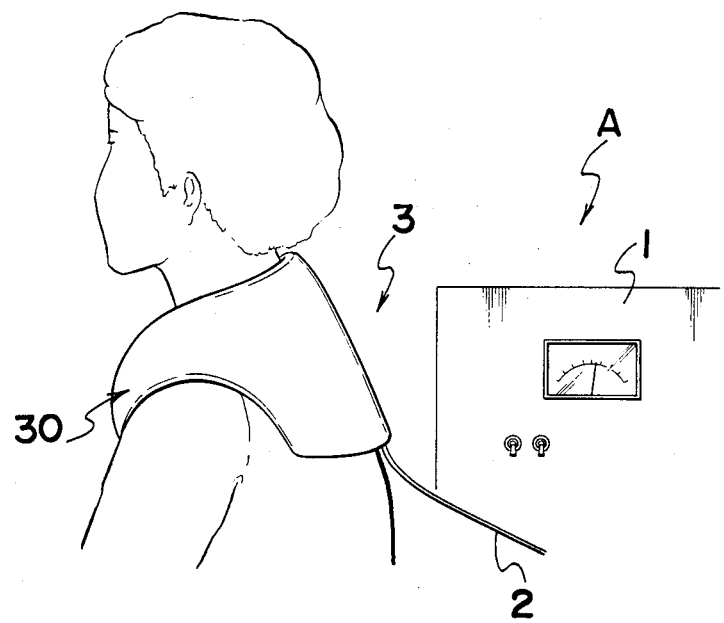
FIG. 11 shows how the second embodiment is used.
Figure 12:
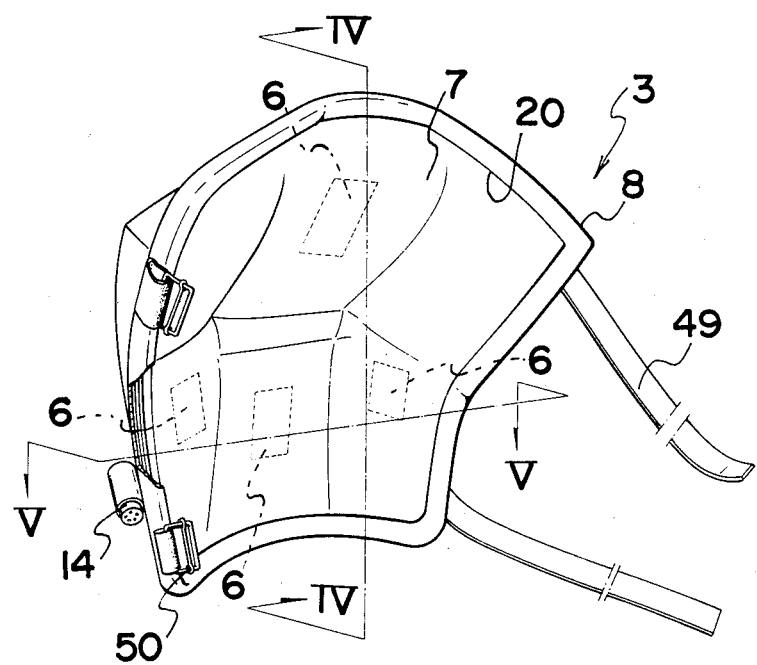
FIG. 12 is a perspective view of the whole portion of a third embodiment of the invention.
Figure 14:
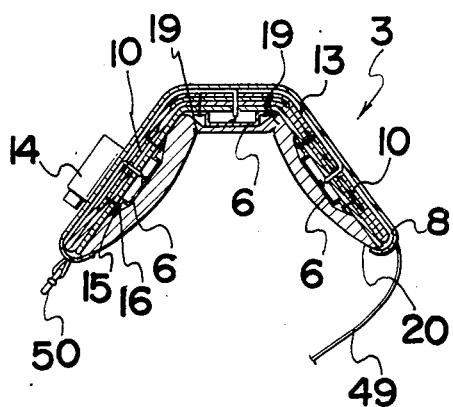
FIG. 14 is a sectional view taken along the line V—V of FIG. 12.
Figure 13:
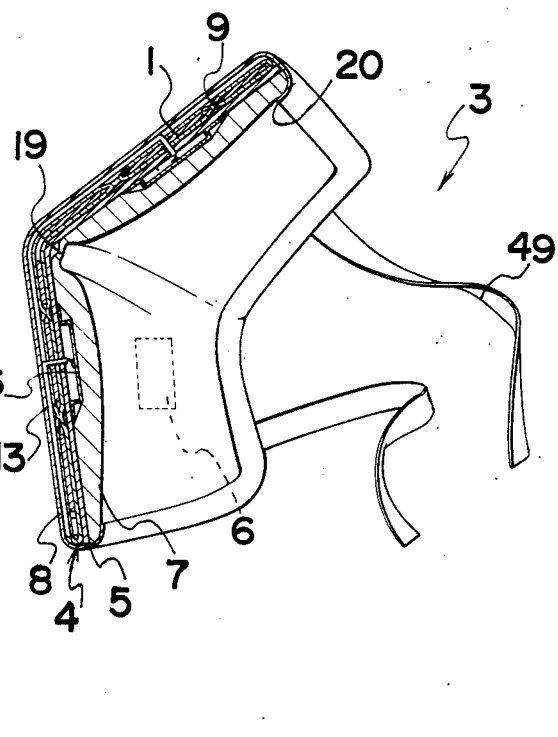
FIG. 13 is a sectional view taken along the line IV—IV of FIG. 12.
Figure 15:
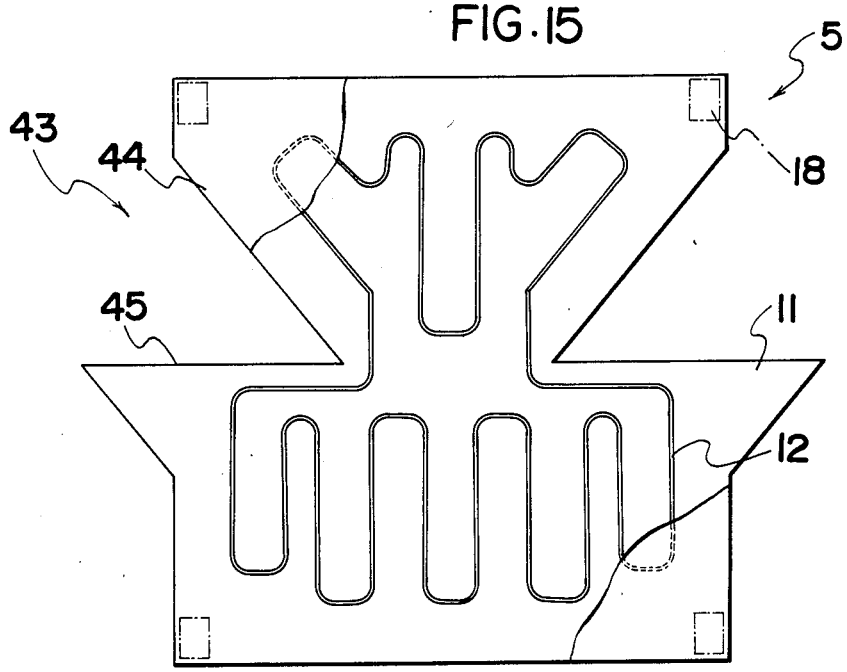
FIG. 15 is a partly cut-away developed view of a heater in the third embodiment.
Figure 16:
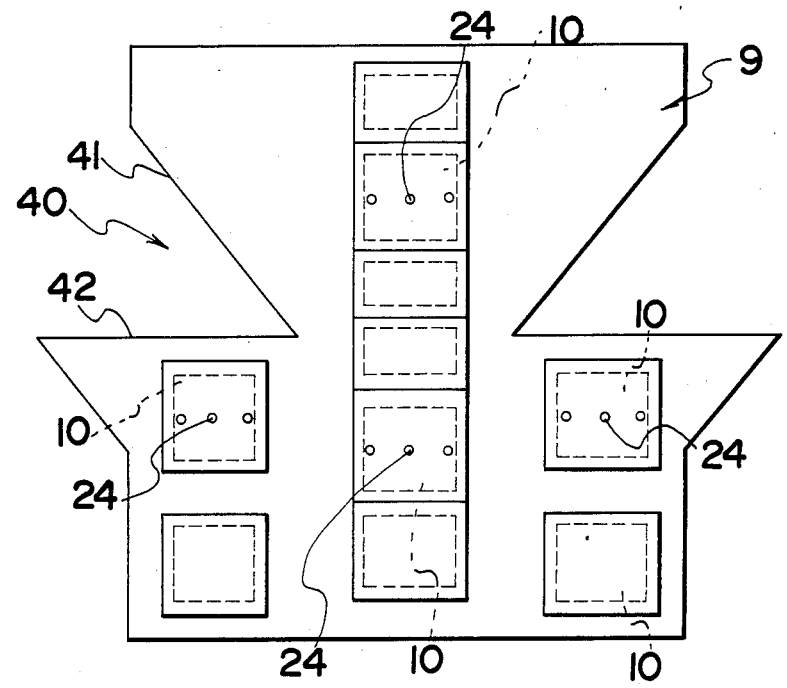
FIG. 16 is a developed view of a mounting plate in the third embodiment.
Figure 17:
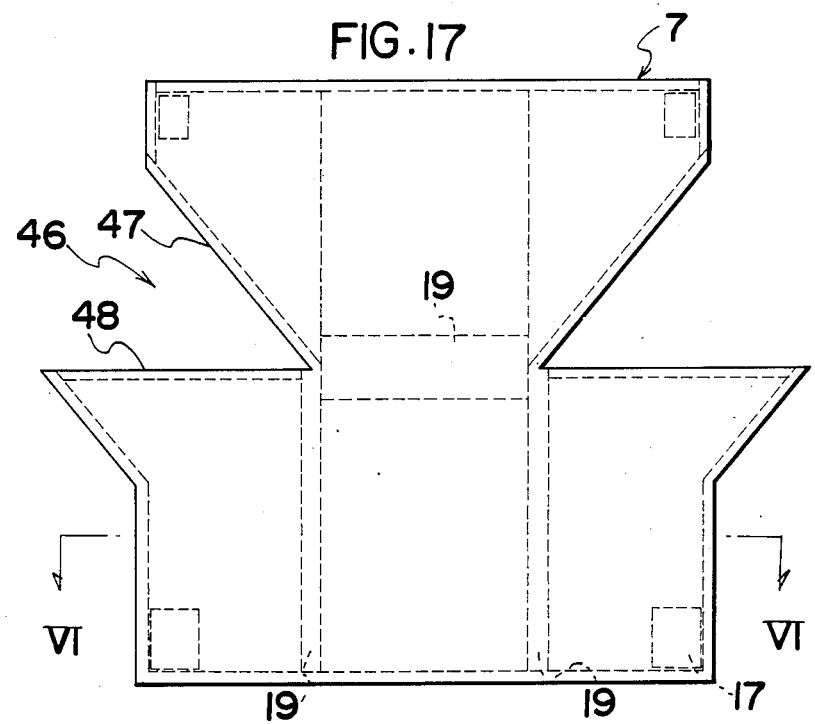
FIG. 17 is a developed view of a wet pack in the third embodiment.
Figure 18:
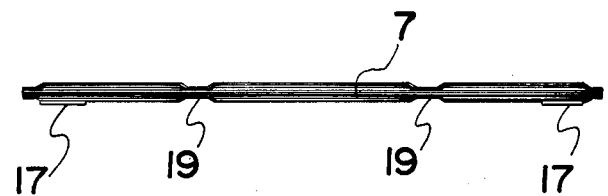
FIG. 18 is a sectional view taken along the line VI—VI of FIG. 17.
Figure 19:
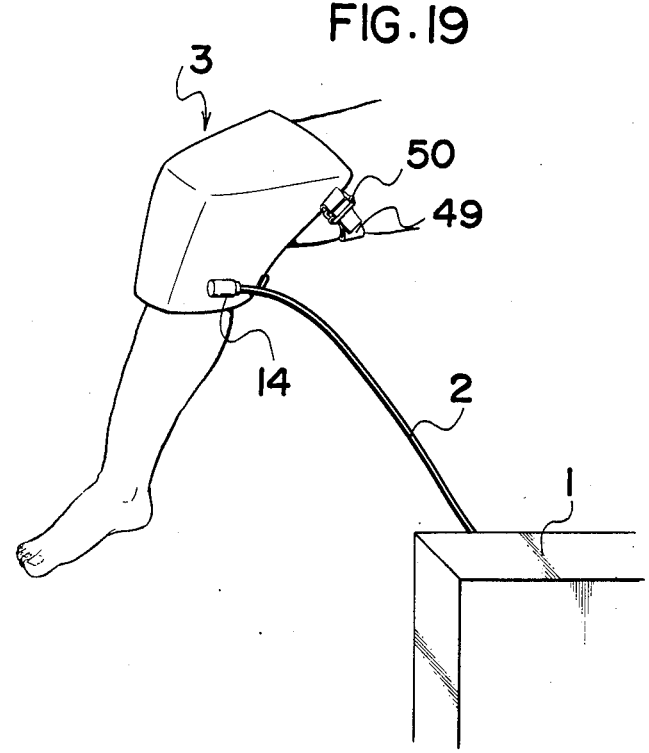
FIG. 19 illustrates the way in which the third embodiment is used.

FIGS. 1 to 4 show a first embodiment, FIGS. 5 to 11 show a second embodiment, FIGS. 12 to 19 show a third embodiment, and FIG. 20 shows the construction of an electrotherapy apparatus embodying the present invention.

Referring first to the first embodiment, a symbol A generally represents a low-frequency electrotherapy apparatus. The low-frequency electrotherapy apparatus includes a main part 1 and a fitting unit 3 connected to the main part 1 through a cable 2. The electrotherapy pack 3 is adapted to be fitted to the affected part of a patient.

The fitting unit 3 includes a mounting substrate 4, heater 5, treating director 6 and a wet pack 7 which are superposed in the mentioned order and covered by a cover 8. The mounting substrate 4 has a substantially square substrate 9 made of a flexible material such as a plastic, and rectangular metal plates 10 which are embedded in the substrate in five columns and five rows. These metal plates 10 are disposed at a constant pitch and the mounting substrate 4 can be flexed to a certain degree at its portions between adjacent metal plates 10. Groves 9' are provided in the substrate 9 between the metal plates 10.

The heater 5 is superposed on the underside of the mounting substrate 4. The heater 5 includes a substantially square heater cover 11 made of a flexible material and accomodating a heater wire 12.

Four rectangular electrodes 6, arranged in two columns and two rows, are disposed on the underside of the heater 5. Each electrode 6 has a substantially U-shaped cross-section. Four cords 13 disposed on the upper side of the mounting substrate 4 are connected at their ends to the inner side of the electrodes 6. The distal ends of the cords 13 extend through the mounting substrate 4 and the heater 5, while the proximal ends of the cords 13 are concentrated into a connector 14 provided on the upper side of the mounting substrate 4. The cords 13 extend through the cord insertion hole 24 formed in the central parts of the metal plates 10. They then extend through the mounting substrate 4.

The electrodes 6 are secured at their lateral extensions 15 to the metal plates 10 in the mounting substrate 4 by means of bolts 16. The bolts 16 are screwed to the metal plates 10 through bolt holes formed in the heater 5, the heater 5 also is supported by the metal plates 10 through the electrode 6.

The wet pack 7 is disposed beneath the heater 5 and the electrode 6. The wet pack 7 has a generally rectangular form, with fastener tapes 17 secured to four corners thereof. These fastener tapes 17 are adapted to cooperate with fastener tapes 18 provided on four corners of the heater 5 thereby detachably fasten the wet pack 7 to the heater 5. The wet pack 7 has a laminated structure composed of a plurality of layers of flannel and a cotton cloth covering these layers. The wet pack 7 thus constructed is compressed from its upper and lower sides so that thin-walled portions 19 crossing each other at right angles are formed.

The cover 8 is provided at its lower side with an opening 20 through which the wet pack 7 is exposed.

In the drawings, the reference numeral 21 designates a lap plate which has a rectangular plate member 22 made of a flexible material such as a plastic, and rectangular lap pieces embedded in the plate member 22 in five columns and five rows. The lap pieces 23 are arranged at a constant pitch, and the plate member 22 is flexible to some extent by the flexing at their portions between adjacent lap pieces 23,23.

The construction of the first embodiment of the invention has been described. This embodiment can be used in a way which will now be explained.

The wet pack 7 is wetted by warm or hot water and is secured to the underside of the heater 5. Then, the electrotherapy pack 3 is placed on the affected part such as the back or the waist of a patient who is lying on his face, such that the wet pack contacts the affected part. Then, the lap plate 21 is placed on the electrotherapy pack 3 so that the electrotherapy pack 3 is bent and curved to conform with the curvature of the affected part due to the weight of the lap plate 21, thereby ensuring a close fit of the wet pack 7 to the affected part. Thus, the fitting unit can be fitted to the affected part in one simple operation.

Then, the main part 1 of the electrotherapy apparatus is operated such that electric current flows between two electrodes 6 which are disposed on a diagonal line of the fitting unit 3. Electric current is supplied from one electrode to the other through the wet pack 7 and the affected part, thereby supplying low-frequency energy to the affected part. This low-frequency energy electrically stimulates the affected part so that the metabolism of living cells is promoted to cure the affected part. By maintaining a constant temperature of the wet pack 7 with the heater 5, the efficiency of the treatment is increased due to combined effects of the electric stimulus and heat.

Also, the comfort of the patient is improved because the electric stimulus is applied gently due to the presence of the thin-walled portions 19.

A second embodiment of the invention will be described hereinunder.

The electrotherapy pack 3 of this embodiment has been designed to treat the cervical vertebrae of the patient. Therefore, the construction of this electrotherapy pack is partly changed from that of the first embodiment, although the same constituents are incorporated. To treat the cervical vertebrae, components 30,30, which wrap around the neck having arcuate forms project outward from both sides of the upper region of the electrotherapy pack 3.

To realize such construction, the constituents of the fitting units are modified as follows.

To provide the components 30,30, which wrap around the neck, arcuate extensions 31,31 are formed to extend outward from both lateral sides of an upper portion of the plate 4 of the mounting substrate. Since this embodiment is designed to treat only the cervical vertebrae, the mounting substrate 4 is required only to be flexible enough to be continuously flexed to follow the curvature of the back of the neck. Also, only four metal plates 10 arranged in two columns and two rows enough to secure the electrodes 6, are embedded in the plate 9 of the mounting substrate. The metal plate 10 has a circular form. The heater 5 has a configuration conforming with the mounting substrate 4.

The construction of the electrodes 6, the structure to fix the electrodes, and the structure to connect the cords 13 to the electrodes 6 are materially identical to those in the first embodiment. The positions of the electrodes 6 are so selected that, when the fitting unit 3 is wound around the neck, the upper two electrodes 6 are disposed at both sides of the fourth cervical vertebrae, while the lower two electrodes 6 are positioned at both sides of the seventh cervical vertebrae of the patient. The construction of the wet pack 7 is materially identical to that in the first embodiment.

To constitute the components, 30,30, which wrap around the neck, the cover 8 is provided at its upper portion with arcuate extensions 32,32 projecting laterally therefrom, and fastening tapes 33,34 are connected to the opposing ends of these extensions so that both components which wrap around the neck can be connected to each other at the front of the neck.

The second embodiment is used in the following manner. While the electrotherapy pack 3 is put on the neck to fit around the cervical vertebrae to be treated, the components 30,30, which wrap around the neck are wound around the neck and connected to each other at the front of the neck thus fixing the electrotherapy pack 3 along the cervical vertebrae. Then, the main part 1 of the electrotherapy apparatus is operated such that electric current flows between two directors 6,6 located on each diagonal line. Thus, the affected part of the cervical vertebrae is supplied with electric current in two directions which approximate the diagonal lines.

A third embodiment of the invention will be described hereinunder.

The fitting unit 3 of this embodiment is designed to treat articulated joints such as the shoulder or the knee. To do this, the electrotherapy pack 3 is partially changed from that of the first embodiment, although the same constituents are used. To treat an articulated joint, the electrotherapy pack 3 is concave at its inner side in conformity with the configuration of the articulated joint. The electrotherapy pack 3 is modified to have a vertical section such that it can flex at its middle region.

To realize such a configuration of the electrotherapy pack 3, the constituents of the electrotherapy pack 3 are modified as follows.

The mounting substrate 4 has a rectangular plate member 9 which is provided with wedge-shaped notches 40 extending from both sides to the center thereof at a substantially middle region along the length thereof. By superposing opposing sides 41,42 of the notch 40, the inner surface of the plate member 9 is allowed to have a concave configuration in conformity with the configuration of the articulated joint. The metal plates 10 are arranged in one column at the center of the plate member 9 and in two lines on both sides of the plate member 9, i.e., two upper metal plates and two lower metal plates are disposed at each side of the column of metal plates.

The heater 5 has a configuration conforming with the mounting substrate 4. As in the case of the substrate 4, the opposing sides 44,45 of each wedge-shaped notch 43 formed therein are superposed so that the heater 5 is allowed to have a concave form following the configuration of the articulated joint.

The construction of the electrodes 6, the structure for securing the electrodes 6 and the structure for connecting the electrodes 6 to the cord 13 are materially identical to those in the first embodiment.

The electrodes 6 are arranged on the inner side of the heater 5 at an upper, lower and both lateral regions. When the electrotherapy pack 3 is fitted along an articulate joint, the electrodes 6 are positioned at the upper, lower and both lateral sides of the articulated joint to be treated.

The wet pack 7 has a configuration conforming with that of the mounting substrate 4. As in the case of the substrate 4, the opposing sides 47, 48 of each wedge-shaped notch 46 formed therein are superposed so that the inner side of the wet pack 7 assumes a concave form following the configuration of the articulated joint.

The thin-walled portions 19 in this wet pack 7 are formed in a downwardly diverging manner in the lower half part of the central portion of the wet pack 7. When the wet pack 7 is attached to the heater 5, the thin-walled portions 19 are between the central lower director 6 and both side electrodes 6,6 and between the central upper electrode 6 and the central lower electrode 6.

The cover 8 has an inner surface concave to conform with the configuration of the articulated joint. Connectors 50 for connecting a belt 49 are attached to an upper end region and a lower end region of one edge of the cover 8. With the electrotherapy pack 3 fitting on the affected part such as a shoulder, the belt 49 is extended past the armpit and is connected to the electrotherapy pack 3 through the connectors 50, thus fixing the electrotherapy pack 3 on the affected part.

This embodiment can be used in a manner explained hereinunder. Namely, the electrotherapy pack is placed on the affected part such as the knee and is fixed by means of the belt 49. In this state, the main part 1 of the apparatus is operated to allow electric current to flow between the upper and lower electrodes 6,6 on the electrotherapy pack 3, as well as between the left and right electrodes 6,6. Thus, the affected part is supplied with electric currents both vertically and laterally.

The function of the main part 1 of the low-frequency electrotherapy apparatus is as follows. The main part 3 has an input section 60 in which the patient's history and treatment recorded on a card are read and converted into signals. The input section 60 is connected to a central controller 61 which is composed of a memory device and an information processing device. The central controller 61 in turn is connected to an output section 62 to drive the medical instruments and also to a display section 64 capable of displaying the information in the form of patterns and characters. The output section 62 is connected to a feedback section 63 which in turn is connected to the central controller 61 to allow the latter to perform a feedback control. Thus, the patient can treat himself simply by putting the card into the apparatus.

What is claimed is:

1. A low frequency electrotherapy apparatus comprising a control device for generating a low frequency current and an electrotherapy pack connected to said control device,
    said electrotherapy pack comprising a mounting substrate, a heater, a treating director and a wet pack stacked on said mounting substrate in a sequential manner in that order, and a cover covering said mounting substrate, heater, treating director and wet pack,
    said mounting substrate comprising a square substrate of a flexible plastic material and a plurality of rectangular metal plates embedded in said square substrate at predetermined intervals and a plurality of grooves formed on the surface of said square substrate at a position between said rectangular metal plates for facilitating the flexibility of said square substrate,
    said heater comprising a square heater cover and a heater wire embedded in said heater cover,
    said treating director comprising electrodes having U-shaped cross sections secured to a lower surface of said heater cover of said heater in a laterally and longitudinally spaced apart manner, said electrodes of said treating director protruding downwardly from said lower surface of said heater cover, said treating director being connected with one end of a cable having its other end connected to said control device,
    said wet pack having a laminated structure comprised of a plurality of layers of flannel and a cotton cloth covering said layers,
    said cover being provided at a lower side thereof with an opening through which said wet pack is exposed.

2. A low-frequency electrotherapy apparatus according to claim 1, further comprising a lap plate mounted on an upper surface of said pack, said lap plate comprising a plate member of a flexible plastic material and a plurality of lap pieces serving as weight on a patient so as to make said electrotherapy pack snugly come into contact with a patient.

3. A low-frequency electrotherapy apparatus comprising a control device for generating a low frequency current and an electrotherapy pack connected to said control device,
    said electrotherapy pack comprising a mounting substrate, a heater, a treating director and a wet pack stacked on said mounting substrate in a sequential manner in that order, and a cover covering said mounting substrate, heater, treating director and wet pack,
    said mounting substrate comprising a substrate of a flexible plastic material and a plurality of circular metal plates embedded in said substrate at predetermined intervals,
    said heater being of the shape of said mounting substrate and comprising a heater cover and a heater wire embedded in said heater cover,
    said treating director comprising electrodes having U-shaped cross sections secured to a lower surface of said heater cover of said heater in a laterally and longitudinally spaced apart manner, said electrodes of said treating director protruding downwardly from said lower surface of said heater cover, said treating director being connected with one end of a cable having its other end connected to said control device,
    said wet pack having a laminated structure comprised of a plurality of layers of flannel and a cotton cloth covering said layers,
    said cover being provided at a lower side thereof with an opening through which said wet pack is exposed,
    said mounting substrate having a pair of lateral sides and an upper region and being provided at its upper region with extensions projecting outwardly from both lateral sides thereof so as to constitute neck wrapping portions, whereby said pack can be fitted around the patient's neck along the cervical vertebrae.

4. A low-frequency electrotherapy apparatus comprising a control device for generating a low frequency current and an electrotherapy pack connected to said control device, said electrotherapy pack comprising a mounting substrate, a heater, a treating director and a wet pack stacked on said mounting substrate in a sequential manner in that order, and a cover covering said mounting substrate, heater, treating director and wet pack, said mounting substrate comprising a generally rectangular substrate of a flexible plastic material and a plurality of rectangular metal plates embedded in said rectangular substrate at predetermined intervals and a pair of wedge shaped notches formed in opposite sides of said substrate at a substantially middle region thereof, said heater being of the shape of said mounting substrate and comprising a square heater cover and a heater wire embedded in said heater cover, said treating director comprising electrodes having a U-shaped cross section secured to a lower surface of said heater cover of said heater in a laterally and longitudinally spaced apart manner, said electrodes of said treating director protruding downwardly from said lower surface of said heater cover, said treating director being connected with one end of a cable having its other end connected to said control device, said wet pack having a laminated structure comprised of a plurality of layers of flannel and a cotton cloth covering said layers, said cover being provided at a lower side thereof with an opening through which said wet pack is exposed, said mounting substrate having an inner side and being concave at said inner side, whereby said fitting unit can be fitted around a shoulder, knee or other articulated joint.

* * * * *